US012343354B2

(12) United States Patent
Iguchi et al.

(10) Patent No.: US 12,343,354 B2
(45) Date of Patent: Jul. 1, 2025

(54) INJECTION CONTAINING p-BORONOPHENYLALANINE

(71) Applicant: Stella Pharma Corporation, Osaka (JP)

(72) Inventors: Yoshiya Iguchi, Osaka (JP); Yoshimitsu Katakuse, Osaka (JP); Hideki Nakashima, Osaka (JP)

(73) Assignee: Stella Pharma Corporation, Osaka (JP)

( * ) Notice: Subject to any disclaimer, the term of this patent is extended or adjusted under 35 U.S.C. 154(b) by 630 days.

(21) Appl. No.: 17/753,658

(22) PCT Filed: Sep. 9, 2020

(86) PCT No.: PCT/JP2020/034086
§ 371 (c)(1),
(2) Date: Mar. 10, 2022

(87) PCT Pub. No.: WO2021/049520
PCT Pub. Date: Mar. 18, 2021

(65) Prior Publication Data
US 2022/0280540 A1    Sep. 8, 2022

(30) Foreign Application Priority Data

Sep. 12, 2019   (JP) ................................ 2019-165979

(51) Int. Cl.
| | |
|---|---|
| A61K 31/69 | (2006.01) |
| A61K 9/00 | (2006.01) |
| A61K 41/00 | (2020.01) |
| A61K 47/02 | (2006.01) |
| A61K 47/10 | (2017.01) |
| A61P 35/00 | (2006.01) |

(52) U.S. Cl.
CPC ............ *A61K 31/69* (2013.01); *A61K 9/0019* (2013.01); *A61K 41/0095* (2013.01); *A61K 47/02* (2013.01); *A61K 47/10* (2013.01); *A61P 35/00* (2018.01)

(58) Field of Classification Search
CPC .. A61K 31/69; A61K 9/0019; A61K 41/0095; A61K 47/02; A61K 47/10; A61P 35/00
See application file for complete search history.

(56) References Cited

U.S. PATENT DOCUMENTS

| | | | |
|---|---|---|---|
| 5,492,900 A | 2/1996 | LaHann | |
| 6,169,076 B1 * | 1/2001 | Shull | C07H 1/00 514/23 |

FOREIGN PATENT DOCUMENTS

| | | |
|---|---|---|
| JP | 2008100925 A | 5/2008 |
| JP | 2009/51766 A | 3/2009 |
| JP | 2013173804 A | 9/2013 |
| JP | 5345771 B2 | 11/2013 |
| RU | 2563211 | 6/2006 |
| RU | 2013144037 | 4/2015 |
| WO | 2004030661 A2 | 4/2004 |

OTHER PUBLICATIONS

Silva, Maria Manuela, and Fernando Cebola Lidon. "An overview on applications and side effects of antioxidant food additives." Emir. J. Food Agric 28, No. 12 (2016): 823-832 (Year: 2016).*
Shull, Brian K., David E. Spielvogel, Gerald Head, Ramesh Gopalaswamy, Sabapathy Sankar, and Kevin Devito. Journal of pharmaceutical sciences 89, No. 2 (2000): 215-222.) (Year: 2000).*
Schroeter, Louis C. "Sulfurous acid salts as pharmaceutical antioxidants." Journal of pharmaceutical sciences 50, No. 11 (1961): 891-901 (Year: 1961).*
Ozhegov et al. "Explanatory dictionary of the Russian language: 80,000 words and phrseological expressions / Russian Academy of Sciences", Institute of Russian Language named after V.V. Vinogradova—4th ed., supplemental.—M.:LLC "A Temp", 2006.
Office Action issued in corresponding Russian Application No. 2022109525, dated Dec. 7, 2023.
Office Action issued in corresponding Japanese Patent Application No. 2021545564, dated Feb. 16, 2024.
Office Action issued in corresponding Taiwanese Application No. 109131216, dated Feb. 27, 2024.
International Preliminary Report on Patentability dated Mar. 24, 2022 during examination of International Application No. PCT/JP2020/034086.
International Search Report dated Nov. 24, 2020 during examination of International Application No. PCT/JP2020/034086.
Miyatake et al. "Boron neutron capture therapy of malignant gliomas", Prog Neurol Surg., vol. 32, pp. 48-56, 2018.
Mishima et al. "New thermal neutron capture therapy for malignant melanoma: melanogenesis-seeking 10B Molecule-melanoma cell interaction from in vitro to first clinical trial", Pigment Cell Research, vol. 2, pp. 226-234, 1989.
Stella Chemifa Corporation, Stella Pharma Corp., "Notification of commencement of the world's first trial using accelerator BNCT", News Release, [online], Sep. 6, 2012, [retrieved on Nov. 6, 2020], Internet: <URL:https://www.stellachemifa.co.jp/files/chikenkaishi_20120906.pdf>, in particular, section «About boron isotope enrichment technology», non-official translation.
Ono, Koji et al., "BNCT Boron Neutron Capture Therapy", Radioisotopes, 2012, vol. 61, No. 4, pp. 209-222, ISSN 1884-4111, in particular, p. 210, p. 215, left column.
European Search Report dated Sep. 13, 2023 during examination of European Patent Application No. 20863900.5.

(Continued)

*Primary Examiner* — James H Alstrum-Acevedo
*Assistant Examiner* — Carolyn L. Ladd
(74) *Attorney, Agent, or Firm* — Norton Rose Fulbright US LLP (57) ABSTRACT

An object of the present invention is to provide an injection solution for boron neutron capture therapy. Provided is an injection solution for boron neutron capture therapy, containing p-boronophenylalanine or a pharmaceutically acceptable salt thereof, with a ratio of boron 10 of boron atoms in a compound of 75% or more; a sugar alcohol; an antioxidant; and water, the injection solution having a pH of 6.5 to 7.8 and an osmotic pressure ratio of 1.0 to 1.8, the injection solution being to be administered by intravenous drip injection.

9 Claims, 1 Drawing Sheet

(56) References Cited

OTHER PUBLICATIONS

Official Action (including English translation) issued in corresponding Russian patent application No. 2022109525, mailed Dec. 7, 2023.
Official Action (including English translation) issued in corresponding Taiwanese patent application No. 109131216, mailed May 30, 2024.
Halbert, G. et al: "Improved pharmaceutical stability of a boronphenylalanine mannitol formulation for boron neutron capture therapy", European Journal of Pharmaceutical Sciences, Jan. 23, 2013, vol. 48, No. 4-5, pp. 735-739.
Nedunchezhian, K. et al: "Boron Neutron Capture Therapy—A Literature Review", Journal of Clinical and Diagnostic Research, Dec. 1, 2016, vol. 10, No. 12, pp. ZE01-ZE04.
Singapore Search Report dated Jul. 28, 2023 during examination of related Singapore Appl. No. 11202202258Y.
Zuo, C. S. et al: "Proton nuclear magnetic resonance measurement of pboronophenylalanine (BPA): A therapeutic agent for boron neutron capture therapy", Medical Physics, Jul. 12, 1999, vol. 26, No. 7, pp. 1230-1236.
Official Action (including English translation) issued in corresponding Japanese patent application No. 2021-545564, mailed Jul. 10, 2024.
Official Action (including English translation) issued in corresponding Singapore patent application No. 11202202258Y, dated Nov. 20, 2024.
Schmidt, E. et al., "Physicochemical Investigation of the Influence of Saccharide-Based Parenteral Formulation Excipients on L-p-Boronphenylalanine Solubilisation for Boron Neutron Capture Therapy", J. Pharm. Sci., 101, p. 223, Sep. 14, 2011 (Sep. 14, 2011).
Official Action issued Apr. 23, 2025 in related Australian Patent Application No. 2020347682, 3 pgs.
Official Action issued Mar. 18, 2025 in related Canadian Patent Application No. 3,151,009, 6 pgs.

\* cited by examiner

INJECTION CONTAINING p-BORONOPHENYLALANINE

This application is a national phase application under 35 U.S.C. § 371 that claims priority to International Application No. PCT/JP2020/034086 filed Sep. 9, 2020, which claims priority to Japan Patent Application No. 2019-165979 filed Sep. 12, 2019, all of which are incorporated herein by reference in their entirety.

BACKGROUND OF THE INVENTION

Technical Field

The present invention relates to an injection solution containing p-boronophenylalanine.

Background

Recently, attention has been drawn to a boron neutron capture therapy (BNCT) as a cancer treatment method utilizing a radioisotope. The boron neutron capture therapy is a treatment method in which a boron compound containing boron-10 isotope ($^{10}B$) is delivered to cancer cells and the cancer cells are irradiated with a low energy neutron (for example, epithermal neutrons), and thus the cancer cells are locally destroyed by a nuclear reaction which arises in the cells. In this treatment method, since it is important to cause a boron compound which contains boron 10 to be selectively accumulated by cells of cancerous tissue so as to enhance therapeutic effect, it is necessary to develop boron compounds which are selectively and certainly taken by cancer cells.

Boron-containing compounds in which boron atoms or boron atomic groups are introduced into a basic structure have been synthesized as an agent used in BNCT. Examples of an agent used in the actual clinical practice include p-boronophenylalanine (BPA) and mercaptoundecahydrododecaborate (BSH).

p-Boronophenylalanine has very poor solubility at physiological pH.

In order to improve solubility of p-boronophenylalanine in water, a method of producing a fructose complex of p-boronophenylalanine (for example, Patent Document 1), and a method of adding a monosaccharide or a polyol to p-boronophenylalanine in an alkaline solution (such as an aqueous sodium hydroxide solution) and removing an inorganic salt with an ion exchange resin for use (for example, Patent Document 2) have been attempted.

Furthermore, another technique for improving solubility of p-boronophenylalanine has been proposed (Patent Document 3).

PRIOR ART DOCUMENT

Patent Documents

Patent Document 1: U.S. Pat. No. 5,492,900
Patent Document 2: U.S. Pat. No. 6,169,076
Patent Document 3: JP-B-5345771

SUMMARY OF THE INVENTION

However, blood boron concentration at the time of administration required for exerting an effect as boron neutron capture therapy is limited. Therefore, it is necessary to adjust the blood boron concentration within a certain range and to strictly determine administration rate. On the other hand, it is desired to establish a well-balanced prescription that does not cause adverse events during administration while maximizing an effect on a subject.

Therefore, an object of the present invention is to provide an injection solution containing p-boronophenylalanine, which has excellent stability, also assures safety as an intravenous drip infusion, and has a small burden on a subject to be administered.

The present inventors have intensively studied to solve the above problems and, as a result, have found that a preparation with excellent effect on a subject can be prepared while enhancing solubility of p-boronophenylalanine in an injection solution, stability in a wide temperature range, and safety, by controlling a ratio of boron 10 of boron atoms in a compound, further, containing a sugar alcohol and an antioxidant, and adjusting pH value and osmotic pressure ratio, and thus the present invention has been completed.

That is, the present invention provides the following injection solutions.

[1]
An injection solution for boron neutron capture therapy, containing:
p-boronophenylalanine or a pharmaceutically acceptable salt thereof, with a ratio of boron 10 of boron atoms in a compound of 75% or more;
a sugar alcohol;
an antioxidant; and
water,
the injection solution having a pH of 6.5 to 7.8 and an osmotic pressure ratio of 1.0 to 1.8,
the injection solution being to be administered by intravenous drip injection.

[2]
The injection solution for boron neutron capture therapy according to [1], which is for being administered at a rate of 150 to 250 mg/kg/hour, as a p-boronophenylalanine concentration, for 1.5 to 3 hours, and then deceleratingly administered at a rate of 80 to 120 mg/kg/hour for 0.5 to 1.5 hours, while irradiating an epithermal neutron ray during the decelerating administration.

[3]
The injection solution for boron neutron capture therapy according to [1] or [2], wherein the sugar alcohol is sorbitol or mannitol.

[4]
The injection solution for boron neutron capture therapy according to any one of [1] to [3], wherein a concentration of the sugar alcohol is 2.6 to 6.5 w/v %.

[5]
The injection solution for boron neutron capture therapy according to any one of [1] to [4], wherein a content ratio of the sugar alcohol is in a range of 0.9 to 3.0, in molar ratio, with respect to a content of p-boronophenylalanine.

[6]
The injection solution for boron neutron capture therapy according to any one of [1] to [5], wherein the antioxidant is sulfite.

[7]
The injection solution for boron neutron capture therapy according to [6], wherein a concentration of the antioxidant is 0.01 to 0.6%.

[8]
The injection solution for boron neutron capture therapy according to [6] or [7], wherein the sulfite is sodium pyrosulfite, sodium sulfite, or sodium bisulfite.

[9]

The injection solution according to any one of [1] to [8], for treating solid cancer.

The injection solution of the present invention has excellent stability, also assures safety as an intravenous drip infusion, and has good properties also for administration to humans and animals.

DETAILED DESCRIPTION OF THE PREFERRED EMBODIMENTS

The unit "mass %" herein is synonymous with "g/100 g". "W/v %" is synonymous with "g/100 ml".

The injection solution of the present invention is an injection solution for boron neutron capture therapy (BNCT), containing p-boronophenylalanine or a pharmaceutically acceptable salt thereof, with a ratio of boron 10 of boron atoms in a compound of 75% or more;
 a sugar alcohol;
 an antioxidant; and
 water, and having a pH of 6.5 to 7.8 and an osmotic pressure ratio of 1.0 to 1.8, which is to be administered by intravenous drip.

[Injection Solution for Boron Neutron Capture Therapy (BNCT)]

(p-Boronophenylalanine or Pharmaceutically Acceptable Salt Thereof)

The p-boronophenylalanine used in the present invention has a ratio of boron 10 of boron atoms in a compound of 75% or more, preferably 80% or more, more preferably 90% or more, even more preferably 95% or more, and particularly preferably 99% or more.

In natural boron (boron), boron 10 and boron 11 are isotopes, and boron 10 is present in a ratio of 20% and boron 11 in a ratio of 80%. Therefore, prior to production of the injection solution containing p-boronophenylalanine of the present invention, boron having a mass number of 10 (boron 10) is concentrated. For this purpose, boron 10 and boron 11 in a natural boron compound are sorted out, and highly concentrated boron 10 is produced. As the boron used in the present invention, boron 10 may be concentrated to increase the concentration of boron 10, or a commercially available product may be used. As the commercially available product, for example, $^{10}$B concentrated boric acid (manufactured by Stella Chemifa Corporation) can be used as a starting material.

Here, as a method for measuring boron 10, it can be performed using Agilent 7500 (manufactured by Agilent), by a quadrupole ICP-MS (ICP-QMS) method using a quadrupole mass spectrometer part. ICP-QMS used for measurement is adjusted according to JIS K0133.

L-form is currently used as p-boronophenylalanine, and L-p-boronophenylalanine can be also preferably used in the present invention, but the present invention is not limited thereto. That is, racemic p-boronophenylalanine containing D-form or both D-form and L-form can be used in the present invention.

Here, p-boronophenylalanine is, for example, synthesized by a known method, after obtaining boron with an increased ratio of boron 10 or after obtaining boric acid with an increased ratio of boron 10 (for example, H. R. Synder, A. J. Reedy, W. M. J. Lennarz, J. Am. Chem. Soc., 1958, 80, 835: C. Malan, C. Morin, SYNLETT, 1996, 167: U.S. Pat. No. 5,157,149: JP-A-2000-212185: and JP-B-2979139), and can be used.

Here, the salt is not particularly limited as long as it is pharmacologically acceptable. Examples of the p-boronophenylalanine salt include salts with an organic acid, salts with an inorganic acid, salts with an organic base, and salts with an inorganic base.

Examples of the salts with an organic acid include acetates, trifluoroacetates, fumarates, maleates, lactates, tartrates, citrates, and methanesulfonates. Examples of the salts with an inorganic acid include hydrochlorides, sulfates, nitrates, hydrobromides, and phosphates. Examples of the salts with an organic base include salts with triethanolamine. Examples of the salts with an inorganic base include ammonium salts, sodium salts, potassium salts, calcium salts, and magnesium salts.

In the injection solution of the present invention, a content of p-boronophenylalanine or a salt thereof based on a total amount of the injection solution is appropriately set depending on a balance with other components. The total content of p-boronophenylalanine and/or a salt thereof based on the total amount of the injection solution is not particularly limited, but is preferably 2.0 to 5.5 w/v %, more preferably 2.5 to 5.0 w/v %, and further preferably 2.5 to 4.0 w/v %.

When the content of p-boronophenylalanine in the injection solution of the present invention is within the above ranges, the amount of the injection solution falls within an appropriate liquid amount during clinical application, solution stability is good, and an effect during administration is excellent.

(Sugar Alcohol)

A sugar alcohol used in the present invention is not particularly limited as long as it is used as a component of an injection in a pharmaceutical field. The sugar alcohol is not limited, but is preferably a monosaccharide sugar alcohol is preferable, and particularly preferably sorbitol and/or mannitol.

As sorbitol, D-sorbitol, which is currently approved for use in medicines and whose safety has been confirmed, can be preferably used, but is not limited thereto. That is, in the present invention, L-form or a mixture of L-form and D-form can be also used.

As mannitol, D-mannitol, which is currently approved for use in medicines and whose safety has been confirmed, can be preferably used, but is not limited thereto. That is, in the present invention, L-form or a mixture of L-form and D-form can be also used.

The total content of the sugar alcohol used in the injection solution of the present invention depends on blending amounts of other additives, but is preferably 2.0 to 7.0 w/v %, more preferably 2.6 to 6.5 w/v %, and further preferably 2.6 to 4.2 w/v %, based on the total amount of the injection solution.

An amount of sugar alcohol is preferably in a range of 0.9 to 3.0, more preferably 0.9 to 2.0, and further preferably 1.1 to 1.5, in molar ratio, with respect to an amount of p-boronophenylalanine. When the amount of sugar alcohol is within these ranges, precipitation of p-boronophenylalanine can be suppressed and an osmotic pressure ratio can be adjusted appropriately.

(Antioxidant)

An antioxidant used in the present invention is not particularly limited as long as it is used as a component of an injection in the pharmaceutical field. The antioxidant is not limited, but is preferably one or more selected from a group consisting of sulfurous acid, bisulfite, pyrosulfurous acid, nitrous acid, ascorbic acid, L-cysteine, thioglycolic acid, and salts thereof.

Here, examples of the salts of sulfurous acid, bisulfite, pyrosulfurous acid, nitrous acid, ascorbic acid, L-cysteine or thioglycolic acid include alkali metal salts such as sodium salts and potassium salts; alkaline earth metal salts such as calcium salts and magnesium salts; and inorganic salts such as aluminum salts and ammonium salts. Furthermore, for example, a salt with an organic base such as trimethylamine, triethylamine, pyridine, picoline, ethanolamine, diethanolamine, triethanolamine, dicyclohexylamine or N,N'-dibenzylethylenediamine can also be used. Particularly preferred are the sodium salts, potassium salts, or ammonium salts.

Particularly preferred as the antioxidant used in the present invention is one or more selected from a group consisting of sodium sulfite, dried sodium sulfite, potassium sulfite, calcium sulfite, sodium bisulfite, potassium bisulfite, ammonium bisulfite, sodium pyrosulfite, and potassium pyrosulfite.

The total content of the antioxidant used in the injection solution of the present invention depends on the blending amounts of other additives, but is preferably 0.005 to 2.0 w/v %, more preferably 0.005 to 1.5 w/v %, further preferably 0.005 to 1.2 w/v %, even more preferably 0.01 to 0.6 w/v %, and most preferably 0.01 to 0.03 w/v %, based on the total amount of the injection solution.

(Water)

The injection solution of the present invention further contains water. A water used in the present invention is not particularly limited as long as it is used as a component of an injection in the pharmaceutical field.

A content of water used in the injection solution of the present invention depends on the blending amounts of other additives, but is preferably 80 w/v % or more and more preferably 85 w/v % or more, and preferably 95 w/v % or less and further preferably 94 w/v % or less, based on the total amount of the injection solution.

(pH)

The pH of the injection solution of the present invention is preferably a pH around neutral to weakly alkaline, in consideration of a balance between in vivo administration and stability. More specifically, the pH is in a range of 6.5 to 7.8 and more preferably 7.0 to 7.8, and particularly from the viewpoint of long-term stability in a low temperature region, preferably in a range of pH exceeding 7.4 and 7.8 or less, and particularly preferably in a vicinity of pH exceeding 7.5 and 7.8 or less. A suitable pH adjusting agent, buffer and the like used in the art may be used to adjust the pH as needed.

(Osmotic Pressure Ratio)

An osmotic pressure ratio of the injection solution of the present invention is not particularly limited, but it is preferably within a range of 1.0 to 1.8 in comparison with physiological saline. More preferably, the osmotic pressure ratio is in a range of 1.1 to 1.5. Within these ranges, it becomes possible to reduce pain, avoid an onset of phlebitis, and shorten administration time in a case of a large amount of intravenous injection.

The injection solution of the present invention may appropriately contain various metal ions that may be contained in vivo, in order to ensure stability in vivo and in vitro. Preferably, sodium ion is contained, and the concentration thereof is not particularly limited, but is particularly preferably from 130 mEq/L to 160 mEq/L. This numerical range which is close to a Na ion concentration range of a body fluid is preferable so that an electrolyte balance between an intracellular fluid and an extracellular fluid is not significantly disturbed.

(pH Adjusting Agent)

The injection solution of the present invention can be appropriately added with a pH adjusting agent such as an inorganic acid such as hydrochloric acid or phosphoric acid or an alkaline component such as sodium hydroxide or potassium hydroxide as needed. Furthermore, it is also preferable to use an organic acid in addition to or in place of the inorganic acid. As the organic acid, citric acid, acetic acid, trifluoroacetic acid, fumaric acid, maleic acid, lactic acid, tartaric acid or methanesulfonic acid is preferably used, and citric acid or lactic acid is further preferably used.

[Other Components]

The injection solution of the present invention may be added with a buffer such as a phosphate buffer solution, a tris-hydrochloric acid buffer solution, an acetate buffer solution, a carbonate buffer solution or a citrate buffer solution as needed. These buffers may be useful in stabilizing a preparation and reducing irritation.

Further, the composition of the present invention can contain other components usually used in the technical field of the present invention as needed, unless contrary to the object of the present invention. Examples of such a component include additives usually used in a liquid, particularly an aqueous composition, for example, preservatives such as benzalkonium chloride, potassium sorbate and chlorohexidine hydrochloride, stabilizer such as edetic acid Na, thickening agents such as hydroxyethylcellulose and hydroxypropylmethylcellulose, isotonizing agents such as sodium chloride, potassium chloride, glycerin, sucrose and glucose, surfactants such as polysorbate 80 and polyoxyethylene hydrogenated castor oil, isotonic agents such as sodium chloride, potassium chloride and glycerin, and pH adjusting agents such as sodium hydroxide.

When the injection solution of the present invention is used as a medicine, it may be in a form of an injection for intravenous injection using a solution. In particular, it may be an intravenous drip injection solution.

The injection solution is produced by dissolving, suspending or emulsifying a certain amount of an active ingredient in an aqueous solvent (for example, distilled water for injection, physiological saline, Ringer's solution, etc.), an oily solvent (for example, vegetable oil such as olive oil, sesame oil, cottonseed oil or corn oil, propylene glycol, etc.)

or the like, together with a dispersant (for example, polysorbate 80, polyoxyethylene hydrogenated castor oil 60, polyethylene glycol, carboxymethyl cellulose, sodium alginate, etc.), a preservative (for example, methylparaben, propylparaben, benzyl alcohol, chlorobutanol, phenol, etc.), an isotonizing agent (for example, sodium chloride, glycerin, D-mannitol, glucose, etc.) or the like. At this time, additives such as a solubilizing agent (for example, sodium salicylate, sodium acetate, etc.), a stabilizer (for example, human serum albumin, etc.) and a soothing agent (for example, benzyl alcohol, etc.) may be used as desired. Further, an antioxidant, a colorant or the like and other additives may be added as needed.

In addition, a "pharmaceutically acceptable carrier" can also be used. Examples of such substances include solvents, solubilizing agents, suspending agents, isotonizing agents, surfactants, soothing agents and the like in liquid preparations. In addition, preparation additives such as preservatives (antiseptics) and colorants can be used according to a conventional method.

Preferable examples of the "solvent" include alcohols, propylene glycol, macrogol, and the like.

Examples of the solubilizing agent include polyethylene glycol, propylene glycol, benzyl benzoate, trisaminomethane, cholesterol, triethanolamine, sodium carbonate, sodium citrate, and the like.

Preferable examples of the "suspending agent" include hydrophilic polymers such as polyvinyl alcohol, polyvinylpyrrolidone, sodium carboxymethylcellulose, methylcellulose, hydroxymethylcellulose, hydroxyethylcellulose and hydroxypropylcellulose, and the like.

Preferable examples of the "isotonizing agent" include glucose, sodium chloride, glycerin, and the like.

Examples of the "surfactant" include sodium lauryl sulfate, lauryl aminopropionic acid, lecithin, benzalkonium chloride, benzethonium chloride, glyceryl monostearate, and the like.

Preferable examples of the "soothing agent" include benzyl alcohol and the like.

Preferable examples of the "preservative" include paraoxybenzoic acid esters, chlorobutanol, benzyl alcohol, phenethyl alcohol, dehydroacetic acid, sorbic acid, and the like.

[Method for Producing Injection Solution]

A method for producing the injection solution of the present invention is not particularly limited, but as an example, the injection solution can be prepared by mixing a pH adjusting agent such as sodium hydroxide, water and p-boronophenylalanine, and then adding a sugar alcohol. Here, in preparation, the order may be important for more efficient production. Particularly preferably, a mixed solution of water and a pH adjusting agent of an alkaline component such as sodium hydroxide is first prepared, and then p-boronophenylalanine is added and stirred. Thereafter, a sugar alcohol is added and dissolved so that an injection solution can be prepared. By following such a protocol, each component can be efficiently dissolved in a short time, and an excellent injection solution can be efficiently prepared.

Amounts of water, p-boronophenylalanine, sugar alcohol and pH adjusting agent at this time are in accordance with the amounts described in the injection solution for boron neutron capture therapy.

[Neutron Capture Therapy]
(Administration)

As a use of the injection solution of the present invention, utilization as an intravenous drip infusion is preferable, and an intravenous drip infusion to be used for boron neutron capture therapy is particularly preferable. Neutron capture therapy is a method of treating by a strong particle beam (alpha ray, 7Li particle) generated by a nuclear reaction between boron 10 taken into tumor cells and neutrons, and the injection solution of the present invention can be used in this method with particular advantage.

Prior to irradiation, the injection solution of the present invention can be previously administered to a subject or an animal, adjusted so as to collect boron 10 in the tumor, and then irradiated with epithermal neutron rays. Alternatively, prior to irradiation, the injection solution of the present invention can be also previously administered to a subject or an animal, adjusted so as to collect boron 10 in the tumor, and then irradiated with epithermal neutron rays while further continuing administration. A dose of the injection solution of the present invention is not particularly limited, but can be controlled to achieve a preferable intracellular boron concentration. Such a dose is set according to a type or progression of a tumor to be applied, age or weight of the subject and the like, but when the injection solution of the present invention is used for intravenous administration, it is administered by an intravenous drip infusion at a rate of 200 to 500 ml per hour for 1.5 to 4.0 hours, and preferably for 2.0 to 3.6 hours. It is particularly preferable that the administration start timing be continuously from before the start of neutron irradiation to during the irradiation.

For example, without limitation, it is also effective that, to patients with brain tumors or patients with head and neck cancer, the injection solution of the present invention is adjusted so that a p-boronophenylalanine concentration is preferably 150 to 250 mg/kg/hour, and more preferably 200 mg/kg/hour, and administered for preferably 1.5 to 3 hours, and more preferably 2 hours, then deceleratingly administered so that the p-boronophenylalanine concentration is preferably 80 to 120 mg/kg/hour, and more preferably 100 mg/kg/hour, and irradiated with epithermal neutron rays while performing such decelerating administration for a maximum of 0.5 to 1.5 hours, and preferably for a maximum of 1 hour. When the injection solution of the present invention is used, preparation before use is not necessary, and it is also possible to perform a series of administration from a start of administration to an end of decelerating administration with one injection solution.

Concerning p-boronophenylalanine by administration, a concentration of boron 10 in tumor tissues is 20 ppm ($10^9$ boron 10 atoms per cell) or more and 60 ppm or less, and preferably about 20 ppm or more and 45 ppm or less. In practice, it is also possible to measure the blood concentration and predict the amount in these tumor tissues or cells.

(Irradiation)

It is preferable to control so that a nuclear reaction of epithermal neutrons efficiently occurs in the tumor cells, and alpha rays and 7Li particles generated by the nuclear reaction can kill only the tumor cells. A dose is calculated based on a blood boron concentration and a neutron fluence irradiated to the tissue, and the dose is multiplied by relative biological effectiveness (RBE) of p-boronophenylalanine so that an X-ray equivalent dose can be calculated.

For example, without limitation, for patients with brain tumors, a skin dose is set to preferably 6 to 12 Gy-Eq, and more preferably about 8.5 Gy-Eq, and irradiation can be performed for about 60 minutes per time at maximum. Alternatively, without limitation, for patients with head and neck cancer, a mucosal dose is set to preferably 10 to 15

Gy-Eq, and more preferably about 12 Gy-Eq, and irradiation can be about 60 minutes per time at maximum.

Action Effect of Present Invention

An antitumor agent of the present invention is highly safe for living bodies and can exhibit a high antitumor effect.

Prior to administration of the injection solution of the present invention, Positron Emission Tomography (PET) can be also used to measure accumulation of p-boronophenylalanine. For example, it is also possible to estimate accumulation of boron compounds by administering, in addition to p-boronophenylalanine, a radioactive compound obtained by labeling p-boronophenylalanine with radionuclide $^{18}$F ($^{18}$F-fluoro-borono-phenylalanine: FBPA), and imaging whole body distribution of the radioactive compound by PET examination. Without limitation, it is particularly preferable to administer to a subject with a boron concentration ratio of cancer tissue/normal tissue of 2.5 or more and preferably 3 or more in such PET examination.

Thus, the injection solution of the present invention is particularly preferably used for neutron capture therapy. A target disease is not limited, but solid cancer is preferable, and cancer originating from epithelial cells (epithelial tumor) can be particularly preferable. Typically, the target disease can be skin cancer including melanoma or the like, lung cancer, breast cancer, stomach cancer, colon cancer, uterine cancer, ovarian cancer, or head and neck cancer (oral cancer, laryngeal cancer, pharyngeal cancer, tongue cancer, etc.). Alternatively, even a sarcoma originating from non-epithelial cells can be targeted. Typically, a target sarcoma can be osteosarcoma, chondrosarcoma, rhabdomyosarcoma, leiomyosarcoma, fibrosarcoma, liposarcoma, and angiosarcoma. In addition to these, brain tumors such as glioma, primary central nervous system malignant lymphoma, meningioma, pituitary adenoma, schwannoma and craniopharyngioma can be target diseases for treatment. Not only initial and single cancer, but also cancer that has spread to individual organs, metastatic cancer, and intractable cancer can be targeted.

The present invention provides the following each embodiment of injection solutions.

[1]
An injection solution for boron neutron capture therapy, containing:
  p-boronophenylalanine or a pharmaceutically acceptable salt thereof, with a ratio of boron 10 of boron atoms in a compound of 75% or more;
  a sugar alcohol;
  an antioxidant; and
  water,
  the injection solution having a pH of 6.5 to 7.8 and an osmotic pressure ratio of 1.0 to 1.8,
  the injection solution being to be administered by intravenous drip injection.

[2]
The injection solution for boron neutron capture therapy according to [1], which is for being administered at a rate of 150 to 250 mg/kg/hour, as a p-boronophenylalanine concentration, for 1.5 to 3 hours, and then deceleratingly administered at a rate of 80 to 120 mg/kg/hour for 0.5 to 1.5 hours, while irradiating an epithermal neutron ray during the decelerating administration.

[3]
The injection solution for boron neutron capture therapy according to [1] or [2], wherein the sugar alcohol is sorbitol or mannitol.

[4]
The injection solution for boron neutron capture therapy according to any one of [1] to [3], wherein a concentration of the sugar alcohol is 2.6 to 6.5 w/v %.

[5]
The injection solution for boron neutron capture therapy according to any one of [1] to [4], wherein a content ratio of the sugar alcohol is in a range of 0.9 to 3.0, in molar ratio, with respect to a content of p-boronophenylalanine.

[6]
The injection solution for boron neutron capture therapy according to any one of [1] to [5], wherein the antioxidant is sulfite.

[7]
The injection solution for boron neutron capture therapy according to [6], wherein a concentration of the antioxidant is 0.01 to 0.6%.

[8]
The injection solution for boron neutron capture therapy according to [6] or [7], wherein the sulfite is sodium pyrosulfite, sodium sulfite, or sodium bisulfite.

[9]
The injection solution for boron neutron capture therapy according to [1] to [8], further comprising a pH adjusting agent.

[10]
The injection solution for boron neutron capture therapy according to [9], wherein the pH adjusting agent is a hydrochloric acid.

[11]
The injection solution for boron neutron capture therapy according to [1] to [10], wherein the injection solution is in a range of pH exceeding 7.5 and 7.8 or less.

[12]
The injection solution according to any one of [1] to [11], for treating solid cancer.

[13]
The injection solution according to any one of [1] to [12], wherein the solid cancer is head and neck cancer or brain tumor.

[14]
The injection solution according to any one of [1] to [13], wherein the p-boronophenylalanine has a ratio of boron 10 of boron atoms in a compound of 90% or more.

[15]
The injection solution according to any one of [1] to [14], wherein the p-boronophenylalanine has a ratio of boron 10 of boron atoms in a compound of 90% or more.

[16]
The injection solution according to any one of [1] to [15], further comprising an organic acid.

[17]
The injection solution according to any one of [1] to [16], wherein the organic acid is citric acid or lactic acid.

EXAMPLES

Hereinafter, the present invention will be described in more detail with reference to Examples, but these do not limit the scope of the present invention.

Production Example

Prior to production of an injection solution containing p-boronophenylalanine (BPA; L-form was used here), $^{10}$B concentrated boric acid, in which the content of $^{10}$B is 96% (manufactured by Stella Chemifa Corporation) obtained by concentrating boron with a mass number of 10 (boron 10) was used. Using the highly concentrated boron 10 thus obtained, p-boronophenylalanine was produced by a conventional method.

Examples 1 to 68

(Preparation of Aqueous BPA Sorbitol Solution)

An aqueous solution containing 2.5 w/v % to 5.0 w/v % BPA and D-sorbitol, sodium bisulfite or sodium pyrosulfite was prepared as follows. That is, first, 5 g to 10 g of BPA was suspended in a solution prepared by dissolving 1.05 to 2.08 g of sodium hydroxide in 175 ml of water. 5.25 to 13.0 g of D-sorbitol was added thereto, and the mixture was stirred to dissolve the D-sorbitol. 0.02 g of sodium bisulfite or sodium pyrosulfite was added to the mixture and dissolved, and 1.22 ml (at pH 7.6) or an appropriate amount of 1 mol/l hydrochloric acid was added to adjust pH, and water was added to make a total amount of 200 ml.

Then, the resulting solution was filtered with a 0.2 μm filter. A composition, osmotic pressure ratio, and pH of each aqueous solution are as shown in Tables 1 and 2.

(Preparation of Aqueous BPA Mannitol Solution)

Aqueous solutions shown in Table 2 were prepared in the same manner as the aqueous BPA sorbitol solution, using mannitol instead of sorbitol. A composition, osmotic pressure ratio, and pH of each aqueous solution are as shown in Table 2.

(Preparation of Aqueous BPA Sugar Alcohol Solution)

Aqueous solutions shown in Table 2 were prepared in the same manner as the aqueous BPA sorbitol solution, allowing to coexist mannitol in addition to sorbitol. A composition, osmotic pressure ratio, and pH of each aqueous solution are as shown in Table 2.

Comparative Example 1

(Preparation of Aqueous L-BPA-Fructose Solution)

L-BPA and fructose were added to water to similarly prepare an aqueous L-BPA-fructose solution.

<Stability Test 1>

Stability evaluation was carried out mainly using the following models and conditions as standard conditions for medicine severe stability test based on ICH guidelines.

First, as stability test 1, a storage test at 40° C. was performed. In this storage test, the aqueous solutions were placed in storage device: LH21-13M (manufactured by NAGANO SCIENCE CO., LTD.), at 40° C.±2° C., 75±5% RH, in a dark place, for 2 weeks and 4 weeks, each solution was sampled, and BPA concentration, Tyr concentration, Phe concentration, and Ac-BPA concentration (high-performance liquid chromatograph Nexera X2 series, manufactured by Shimadzu Corporation) were measured and compared with those at the start of the test.

Here, measurement conditions by HPLC are as follows.

Column used: Mightysil RP-18GP (5 μm, 4.6×150 mm) manufactured by KANTO CHEMICAL CO., INC.

Mobile phase: 0.05 mol/L sodium dihydrogen phosphate reagent solution (pH 2.5)/methanol (95:5)

Column temperature: Constant temperature around 40° C.

Flow rate: about 0.8 ml/min

Injection volume: 10 μl

Detection wavelength: 223 nm

Compositions of Examples and results of stability evaluation 1 are shown in Tables 1 and 2. BPA residual amounts in the tables indicate residual amounts of BPA after 4 weeks from storage when the amount of BPA used for production in stability test 1 was 100%. Although not shown in the tables, an amount of initial tyrosine was evaluated as an index showing a state of initial BPA decomposition due to coexistence of components other than BPA in the composition.

TABLE 1

| Examples | BPA Concentration | Additive 1 | Additive 2 | Measured osmotic pressure ratio | Measured PH | BPA Residual amount after 4 weeks |
|---|---|---|---|---|---|---|
| Example 1 | 2.5% | Sorbitol | Sodium | 1.0 | 7.4 | 99% or more |
| Example 2 | | 2.625% | bisulfite | 1.0 | 7.6 | |
| Example 3 | | | 0.01% | 1.0 | 7.8 | |
| Example 4 | 3.5% | Sorbitol | | 1.5 | 7.4 | |
| Example 5 | | 3.675% | | 1.5 | 7.6 | |
| Example 6 | | | | 1.4 | 7.8 | |
| Example 7 | 4.0% | Sorbitol | | 1.7 | 7.4 | |
| Example 8 | | 4.2% | | 1.6 | 7.6 | |
| Example 9 | | | | 1.6 | 7.8 | |
| Example 10 | 2.5% | Sorbitol | Sodium | 1.0 | 7.4 | 99% or more |
| Example 11 | | 2.625% | pyrosulfite | 1.0 | 7.6 | |
| Example 12 | | | 0.01% | 1.0 | 7.8 | |
| Example 13 | 3.5% | Sorbitol | | 1.5 | 7.4 | |
| Example 14 | | 3.675% | | 1.4 | 7.6 | |
| Example 15 | | | | 1.4 | 7.8 | |
| Example 16 | 4.0% | Sorbitol | | 1.7 | 7.4 | |
| Example 17 | | 4.2% | | 1.6 | 7.6 | |
| Example 18 | | | | 1.6 | 7.8 | |
| Example 19 | 3.0% | Sorbitol | Sodium | 1.2 | 7.4 | 99% or more |
| Example 20 | | 3.15% | bisulfite | 1.2 | 7.6 | |
| Example 21 | | | 0.01% | 1.2 | 7.8 | |
| Example 22 | 3.0% | Sorbitol | | 1.6 | 7.4 | |
| Example 23 | | 4.7% | | 1.5 | 7.6 | |
| Example 24 | | | | 1.5 | 7.8 | |
| Example 25 | 3.0% | Sorbitol | | 1.8 | 7.4 | |
| Example 26 | | 5.75% | | 1.7 | 7.6 | |
| Example 27 | | | | 1.8 | 7.8 | |
| Example 28 | 3.0% | Sorbitol | Sodium | 1.2 | 7.4 | 99% or more |
| Example 29 | | 3.15% | pyrosulfite | 1.2 | 7.6 | |
| Example 30 | | | 0.01% | 1.2 | 7.8 | |

TABLE 1-continued

| Examples | BPA Concentration | Additive 1 | Additive 2 | Measured osmotic pressure ratio | Measured PH | BPA Residual amount after 4 weeks |
|---|---|---|---|---|---|---|
| Example 31 | 3.0% | Sorbitol 4.7% | | 1.6 | 7.4 | |
| Example 32 | | | | 1.5 | 7.6 | |
| Example 33 | | | | 1.5 | 7.8 | |
| Example 34 | 3.0% | Sorbitol 5.75% | | 1.8 | 7.4 | |
| Example 35 | | | | 1.8 | 7.6 | |
| Example 36 | | | | 1.7 | 7.8 | |
| Example 37 | 3.0% | Sorbitol 4.7% | Sodium bisulfite 0.01% | 1.6 | 7.2 | 99% or more |
| Example 38 | 2.5% | Sorbitol 5.35% | Sodium bisulfite 0.01% | 1.6 | 7.4 | 99% or more |
| Example 39 | | | | 1.6 | 7.6 | |
| Example 40 | | | | 1.6 | 7.8 | |
| Example 41 | 2.5% | Sorbitol 6.5% | | 1.8 | 7.4 | |
| Example 42 | | | | 1.8 | 7.6 | |
| Example 43 | | | | 1.8 | 7.8 | |
| Example 44 | 2.5% | Sorbitol 5.35% | Sodium pyrosulfite 0.01% | 1.6 | 7.4 | 99% or more |
| Example 45 | | | | 1.6 | 7.6 | |
| Example 46 | | | | 1.6 | 7.8 | |
| Example 47 | 2.5% | Sorbitol 6.5% | | 1.8 | 7.4 | |
| Example 48 | | | | 1.8 | 7.6 | |
| Example 49 | | | | 1.8 | 7.8 | |

(% of BPA and additives means w/v %)

As shown in Table 1, the compositions of all the Examples showed good stability. In cases where the BPA concentration was set to 2.5 w/v %, and the sorbitol concentration was increased to 5.35 w/v % or 6.5 w/v %, even when the type and concentration of the antioxidant were verified under the same conditions, compositions showing good stability were similarly obtained.

TABLE 2

| Examples | BPA Concentration | Additive 1 | Additive 2 | Measured osmotic pressure ratio | Measured PH | BPA Residual amount after 4 weeks |
|---|---|---|---|---|---|---|
| Example 50 | 2.5% | Sorbitol 2.625% | Sodium bisulfite 0.2% | 1.1 | 7.6 | 99% or more |
| Example 51 | 2.5% | Sorbitol 2.625% | Sodium bisulfite 0.6% | 1.4 | 7.6 | |
| Example 52 | 2.5% | Sorbitol 2.625% | Sodium bisulfite 1.2% | 1.9 | 7.6 | |
| Example 53 | 2.5% | Sorbitol 2.625% | Sodium pyrosulfite 0.2% | 1.1 | 7.6 | 99% or more |
| Example 54 | 2.5% | Sorbitol 2.625% | Sodium pyrosulfite 0.6% | 1.4 | 7.6 | |
| Example 55 | 2.5% | Sorbitol 2.625% | Sodium pyrosulfite 1.2% | 1.9 | 7.6 | |
| Example 56 | 2.5% | Mannitol 2.625% | Sodium bisulfite 0.01% | 1.0 | 7.8 | 99% or more |
| Example 57 | 2.5% | Mannitol 5.35% | Sodium bisulfite 0.01% | 1.6 | 7.4 | |
| Example 58 | 2.5% | Mannitol 5.35% | Sodium bisulfite 0.01% | 1.6 | 7.6 | |
| Example 59 | 2.5% | Mannitol 5.35% | Sodium bisulfite 0.01% | 1.6 | 7.8 | |
| Example 60 | 2.5% | Sorbitol 2.625% | Sodium bisulfite 0.01% | 1.5 | 7.6 | 99% or more |

TABLE 2-continued

| Examples | BPA Concentration | Additive 1 | Additive 2 | Measured osmotic pressure ratio | Measured PH | BPA Residual amount after 4 weeks |
|---|---|---|---|---|---|---|
| Example 61 | 2.5% | Sorbitol 2.625% | Sodium bisulfite 0.01% | 1.8 | 7.6 | 99% or more |
| Example 62 | 2.5% | Sorbitol 2.625% | Sodium bisulfite 0.01% | 2.1 | 7.6 | 99% or more |
| Example 63 | 2.5% | Sorbitol 1.31% Mannitol 1.31% | Sodium bisulfite 0.01% | 1.0 | 7.6 | 99% or more |
| Example 64 | 2.5% | Sorbitol 2.625% Mannitol 2.625% | Sodium bisulfite 0.01% | 1.6 | 7.6 | |
| Example 65 | 2.5% | Sorbitol 3.25% Mannitol 3.25% | Sodium bisulfite 0.01% | 1.9 | 7.4 | |
| Example 66 | 2.5% | | Sodium bisulfite 0.01% | 1.8 | 7.6 | |
| Example 67 | | | Sodium bisulfite 0.01% | 1.8 | 7.8 | |
| Example 68 | 5.0% | Sorbitol 5.25% | Sodium bisulfite 0.01% | 2.1 | 7.6 | 99% or more |

(% of BPA and additives means w/v %)

In the storage test of the compositions of Table 2 as well, it was found that p-boronophenylalanine was retained in the aqueous solutions of the Examples at 99% or more even after 4 weeks or more. In the retention property observation, no change in components were observed even from change in color and appearance. In Examples 50 to 55, an initial increase in tyrosine content was observed. On the other hand, a fructose preparation remarkably decomposes and changes in color and the BPA concentration is greatly reduced, whereas the injection solutions of the Examples containing sorbitol or mannitol show little change in concentration and are stable.

By comprehensively determining the results of solubility and the storage test, it was found that the injection solutions containing sorbitol or mannitol of the Examples have excellent stability at a pH of 7.4 to 7.8, and 40° C. storage, and also excellent homogeneity of the solution.

Examples 69 to 72

(Preparation of Aqueous BPA Sorbitol Solution)

An aqueous solution containing 3 w/v % BPA, D-sorbitol and sodium bisulfite was prepared as follows. That is, first, 0.62 g of sodium hydroxide was added to 87 ml of water, and the mixture was stirred. 3 g of L-BPA was suspended therein. 3.15 g of D-sorbitol was added thereto, and the mixture was stirred at room temperature for 30 minutes to completely dissolve the D-sorbitol. 0.02 g of sodium bisulfite was added thereto, and an appropriate amount of 1 mol/l hydrochloric acid or 1 mol/l citric acid was added thereto at room temperature to adjust pH, and water was added to make a total amount of 100 ml.

<Stability Test 2>

The thus prepared aqueous BPA sorbitol solution was subjected to stability test 2. In this test, the aqueous BPA sorbitol solution was subjected to a storage test at 5° C. In this storage test, the sample was allowed to stand at 5° C.±3° C./ambH/dark place, and the presence or absence of cloudiness and the time until cloudiness occurred were measured. The results are shown in Table 3.

TABLE 3

| | HCl | Citric acid | pH | Stirring time after pH adjustment | Condition |
|---|---|---|---|---|---|
| Example 69 | 2.5 ml (mmol) | 0 ml (mmol) | 7.0 | 180 min | Clearness → cloudiness was slightly observed after storage at 5° C. for 7 days |
| Example 70 | 0 ml (mmol) | 0.8 ml (mmol) | 7.1 | | Clearness confirmed after storage at 5° C. for 7 days |
| Example 71 | 0 ml (mmol) | 0.8 ml (mmol) | 7.2 | | Clearness confirmed after storage at 5° C. for 7 days |
| Example 72 | 0 ml (mmol) | 0.8 ml (mmol) | 7.4 | | Clearness confirmed after storage at 5° C. for 7 days |

Example 69: HCl 0.09 w/v %

Examples 70-72: Citric acid 0.15 w/v %

As a result, it was found that, in Example 69 in which hydrochloric acid was used as a regulator at a pH of 7.0, cloudiness might occur after storage.

Next, an aqueous solution containing 3 w/v % BPA, D-sorbitol, and sodium bisulfite was prepared as follows. That is, first, 0.32 g of sodium hydroxide was added to 43 ml of water, and the mixture was stirred. 1.50 g of L-BPA was suspended therein. 1.575 g of D-sorbitol was added thereto, and the mixture was stirred at room temperature for 30 minutes to completely dissolve the D-sorbitol. 0.01 g of sodium bisulfite was added thereto, and an appropriate amount of 1 mol/l hydrochloric acid was added thereto at room temperature to adjust pH, and water was added to make a total amount of 50 ml.

TABLE 4

|  | Test Example 1 | Test Example 2 | Test Example 3 | Test Example 4 |
|---|---|---|---|---|
| pH | 6.8 | 7.0 | 7.2 | 7.6 |
| Hydrochloric acid | 19 Hours | 26 Hours | 66 Hours | No cloudiness was observed until 90 hours |

As a result, when hydrochloric acid was used, cloudiness might occur when stored at 5° C., especially in a low pH region. On the other hand, precipitation could be suppressed by adding citric acid instead of hydrochloric acid. In an intravenous injection, the presence (precipitation) of insoluble fine particles poses a problem, but the precipitation can be suppressed even during storage at low temperatures, so that a stable and excellent preparation can be prepared.

<Administration Test for Head and Neck Cancer Subjects>

Using the same aqueous solution as in Example 20 as an injection solution except for adjusting to 0.02 w/v % of sodium bisulfite and an osmotic pressure ratio of 1.3, neutron capture therapy was performed to subjects with 21 cases of head and neck cancer that were ineffective in standard treatment. Prior to administration of the injection solution, Positron Emission Tomography (PET) was used to measure accumulation of p-boronophenylalanine. The radioactive compound labeled obtained by labeling p-boronophenylalanine with radionuclide $^{18}F$ (18F-fluoro-borono-phenylalanine: FBPA) was administered, and the accumulation of boron compounds was estimated by imaging whole body distribution by PET examination. The injection solution was administered to subjects having a boron concentration ratio of cancer tissue/normal tissue of 3 or more by such PET examination.

Prior to irradiation, the injection solution was administered to the subjects in advance. In order that boron 10 will collect in tumors, the injection solution for intravenous administration was adjusted so as to have a BPA concentration of 200 mg/kg/hour for each patient and administered for 2 hours, then deceleratingly administered so as to be 100 mg/kg/hour dose, and epithermal neutron rays were irradiated during the decelerating administration.

Concerning p-boronophenylalanine by administration, it could be confirmed that the blood concentration of boron 10 was about 20 ppm ($10^9$ boron 10 atoms per cell) or more and 45 ppm or less. Thus, the blood concentration was measured, and the amount in these tumor tissues or cells was predicted.

(Irradiation)

Figure 1:
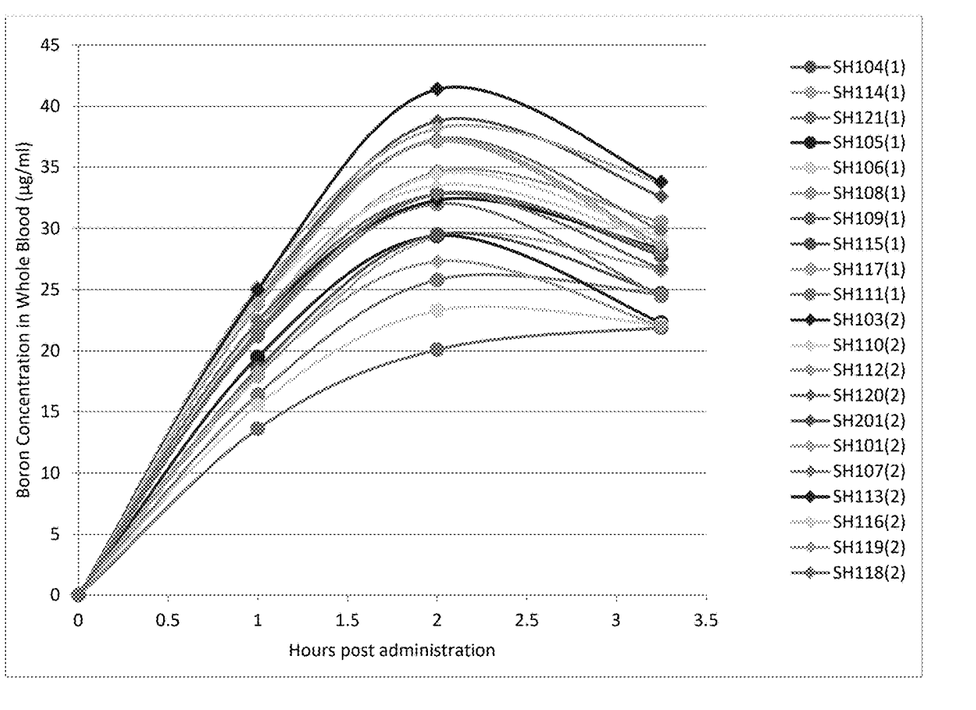
FIG. 1 is a graph depicting $^{10}$B concentration (ppm, vertical axis) versus time (horizontal axis (hr)) in whole blood of each subject after a composition of Example 20 was administered to 21 subjects having head and neck cancer. The composition was administered to the following 21 subjects (10 male subjects and 11 female subjects), and the 1 hour, 2 hour, and 3.25 hour $^{10}$B concentration for each subject are included in brackets after each subject listed. Male subjects include subject SH104(1) [21.6, 32.8, 27.8]; subject SH114(1) [17.9, 29.3, 26.6]; subject SH121(1) [16.4, 25.8, 24.6]; subject SH105(1) [19.5, 29.4, 22.3]; subject SH106(1) [15.5, 23.3, 22.1]; subject SH108(1) [22.5, 34.6, 30.5]; subject SH109(1) [13.6, 20.1, 21.9]; subject SH115(1) [18.5, 29.5, 24.7]; subject SH117(1) [24.6, 37.1, 28.2]; and subject SH111(1) [21.2, 32.0, 24.5]. Female subjects include subject SH103(2) [22.2, 32.3, 28.3]; subject SH110(2) [22.2, 34.4, 29.3]; subject SH112(2) [18.2, 27.3, 22.0]; subject SH120(2) [21.5, 32.8, 28.1]; subject SH201(2) [24.0, 38.8, 32.6]; subject SH101(2) [25.2, 38.2, 33.7]; subject SH107 (2) [24.1, 37.3, 29.8]; subject SH113(2) [25.0, 41.4, 33.8]; subject SH116(2) [23.9, 33.5, 28.9]; subject SH119(2) [23.7, 37.2, 28.6]; and subject SH118(2) [22.4, 32.8, 26.7]. The 1°B concentration for each subject at time of administration (time=0 hours) is 0 ppm.

For each head and neck cancer patient, a mucosal dose was set to about 12 Gy-Eq, and irradiation was performed for about 60 minutes per time at maximum. A graph showing a relationship between a time (horizontal axis (hr)) when the injection solution used in this test was dripped to a subject and a blood concentration of $^{10}B$ (μg/ml) is shown (FIG. 1). Concerning p-boronophenylalanine by administration, the blood concentration of boron 10 was confirmed to be 20 ppm or more and 45 ppm or less, and with regard to particularly effective subjects, it was shown that the values were in this range at a time zone of 2 hours or more and more than 3 hours after the start of administration (FIG. 1).

As a result, first of all, no adverse event during administration of the injection solution was observed in any of the subjects. That is, none of the subjects developed shock symptoms at the time of administration. In addition, phlebitis was not observed after administration. After neutron irradiation, in 15 cases, an effect of tumor reduction could be obtained for 90 days. A 90-day response rate was 71.4%.

<Administration Test for Brain Tumor Subjects>

Using the same aqueous solution as in Example 20 as an injection solution except for adjusting to 0.02% of sodium bisulfite and an osmotic pressure ratio of 1.3, neutron capture therapy was performed to subjects with brain tumors that were ineffective in standard treatment. Prior to administration of the injection solution, Positron Emission Tomography (PET) was used to measure accumulation of p-boronophenylalanine. The radioactive compound labeled obtained by labeling p-boronophenylalanine with radionuclide $^{18}F$ (18F-fluoro-borono-phenylalanine: FBPA) was administered, and the accumulation of boron compounds was estimated by imaging whole body distribution by PET examination. The injection solution was administered to subjects having a boron concentration ratio of cancer tissue/normal tissue of 3 or more by such PET examination.

Prior to irradiation, the injection solution was administered to the subjects in advance. In order that boron 10 will collect in tumors, the injection solution for intravenous administration was adjusted so as to have a BPA concentration of 200 mg/kg/hour for each patient and administered for 2 hours, then deceleratingly administered so as to be 100 mg/kg/hour dose, and epithermal neutron rays were irradiated during the decelerating administration.

Concerning p-boronophenylalanine by administration, it could be confirmed that the blood concentration of boron 10 was about 20 ppm ($10^9$ boron 10 atoms per cell) or more and 45 ppm or less. Thus, the blood concentration was measured, and the amount in these tumor tissues or cells was predicted.

(Irradiation)

For each brain tumor patient, a skin dose was set to about 8.5 Gy-Eq, and irradiation was performed for about 60 minutes per time at maximum.

As a result, first of all, no adverse event during administration of the injection solution was observed in any of the subjects. That is, none of the subjects developed shock symptoms at the time of administration. In addition, phlebitis was not observed after administration. After neutron irradiation, a life extension rate for one year out of 27 cases was 81.5%.

The invention claimed is:

1. An injection solution for boron capture therapy, comprising:
   p-boronophenylalanine or a pharmaceutically acceptable salt thereof, wherein the p-boronophenylalanine or pharmaceutically acceptable salt thereof is enriched in boron-10 such that boron-10 represents at least 75% of a total boron content;
   a sugar alcohol;
   an antioxidant;
   hydrochloric acid; and
   water, wherein the injection solution has a pH of 6.5 to 7.8 and an osmotic pressure ratio of 1.0 to 1.8, and wherein the injection solution is to be administered by intravenous drip injection.

2. The injection solution for boron neutron capture therapy according to claim 1, which is for being administered at a rate of 150 to 250 mg/kg/hour, as a p-boronophenylalanine concentration, for 1.5 to 3 hours, and then deceleratingly administered at a rate of 80 to 120 mg/kg/hour for 0.5 to 1.5 hours, while irradiating an epithermal neutron ray during the decelerating administration.

3. The injection solution for boron neutron capture therapy according to claim 1, wherein the sugar alcohol is sorbitol or mannitol.

4. The injection solution for boron neutron capture therapy according to claim 1, wherein the concentration of the sugar alcohol is 2.6 to 6.5 w/v %.

5. The injection solution for boron neutron capture therapy according to claim 1, wherein the content ratio of the sugar alcohol is in a range of 0.9 to 3.0, in molar ratio, with respect to a content of p-boronophenylalanine.

6. The injection solution for boron neutron capture therapy according to claim 1, wherein the antioxidant comprises a sulfite.

7. The injection solution for boron neutron capture therapy according to claim 6, wherein the concentration of the antioxidant is 0.01 to 0.6 w/v %.

8. The injection solution for boron neutron capture therapy according to claim 6, wherein the sulfite is sodium pyrosulfite, sodium sulfite, or sodium bisulfite.

9. The injection solution according to claim 1, for treating solid cancer.

* * * * *